United States Patent [19]

Yan

[11] Patent Number: 4,981,952
[45] Date of Patent: Jan. 1, 1991

[54] METHOD FOR THE PURIFICATION OF VITAMIN K-DEPENDENT PROTEINS

[75] Inventor: S. Betty Yan, Indianapolis, Ind.
[73] Assignee: Eli Lilly and Company, Indianapolis, Ind.
[21] Appl. No.: 393,281
[22] Filed: Aug. 16, 1989

Related U.S. Application Data

[63] Continuation-in-part of Ser. No. 253,279, Oct. 4, 1988, abandoned.

[51] Int. Cl.[5] ............................ C07K 3/22; C07K 3/28
[52] U.S. Cl. .................................... 530/384; 530/416; 530/412; 530/417; 530/413
[58] Field of Search ............... 530/416, 412, 417, 413, 530/384

[56] References Cited

U.S. PATENT DOCUMENTS

| | | | |
|---|---|---|---|
| 4,512,992 | 4/1985 | Jones et al. | 260/112 |
| 4,518,526 | 5/1985 | Olson | 260/112 |
| 4,599,197 | 7/1986 | Wetzel | 530/405 |
| 4,677,196 | 6/1987 | Rausch et al. | 530/412 |
| 4,734,362 | 3/1988 | Hung et al. | 435/68 |
| 4,766,224 | 8/1988 | Rausch | 530/412 |
| 4,786,726 | 11/1988 | Smith | 530/381 |

OTHER PUBLICATIONS

Scoper, R. K. 1981, *Analytical Biochemistry*, 114: 8–18.
Davier et al., 1981, *Analytical Biochemistry*, 114: 19–27.
Bottenus et al., 1985, Thromb. Haemostasis 54(1):216 (Abstract).
Sudhof et al., 1985, J. Neurochem. 44(4):1302–1307, (Abstract).
Tanaka et al., 1984, Biochem. Biophys. Acta. 787(2):158–164 (Abstract).
Osterman, L. A. 1986, *Methods of Protein and Nucleic Acid* Research vol. 3, *Chromatography*, Springer Verlag, New York, pp. 403–404.
Babu, Y. S. et al. *J. Mol. Biol.* 204:191 (1988).
Stenflo, *The Biochemistry of Protein C* in *Protein C and Related Proteins* 21 (R. M. Bertina ed. 1989).
Fritsche, V. et al., *Biochem. Biophys. Acta* 957:122 (1988).
Cheung, W. Y. *Scientific American* 246:62 (1982).
Kisiel and Davie, Protein C in 80 *Methods in Enzymology* 320 (1981).
Luria, S. E. et al., General Virology 335–337 (3rd ed. 1978).
Jorgensen et al. *J. Biol. Chem.* 262:6729 (1987).
Kaufman et al., *J. Biol. Chem.* 261:9622 (1986).
Church et al., 264:17882 (1989).
Brose, G. J. and Majerus, P. W., 1980, *J. Biol Chem.* 256:1242–1247.
Scopes, R. K. 1987, *In: Protein Purification: Principles and Practice*, 2nd Ed. Springer-Verlag, New York, N.Y., pp. 156–167.
Stenflo, J., 1976, *J. Biol. Chem.* 251:355–363.
Johnson, A. E. et al., 1983, *J. Biol. Chem.* 258:5554–5560.
Ohlin, A. et al., 1988, *J. Biol. Chem.* 263:7411–7417.
Esmon, N. L. et al., 1983, *J. Biol. Chem.* 258:5548–5553.
Yan, S. B. et al., 1989, Poster and Slide Presentation at the UCLA Symposium on Cardiovascular Diseases, Apr. 10–16.
Yan, S. B. et al., 1989, *TIBS* 14:264–268.

Primary Examiner—Margaret Moskowitz
Assistant Examiner—Keith C. Furman
Attorney, Agent, or Firm—Amy E. Hamilton; Leroy Whitaker; Douglas K. Norman

[57] ABSTRACT

The recovery of vitamin K-dependent proteins produced by transformed microorganisms can be effected from the cell culture medium utilizing the changes in the protein which occur in the presence of divalent cations. The present process uses divalent cations to alter the binding affinity of the proteins and thereby selectively elute the proteins away from contaminants in the culture medium using standard chromatography.

47 Claims, 4 Drawing Sheets

Purification Flow Chart

Purification Flow Chart

Elution of HPC with NaCl Gradient from Pharmacia Mono-Q Column

Elution of HPC with CaCl$_2$ Gradient from Pharmacia Mono-Q Column

Elution Profile of rHPC on Fast Flow Q Column

METHOD FOR THE PURIFICATION OF VITAMIN K-DEPENDENT PROTEINS

CROSS-REFERENCE

This application is a continuation-in-part of co-pending U.S. application Ser. No. 07/253,279 filed Oct. 4, 1988, now abandoned.

BACKGROUND

A large number of human and other mammalian proteins, including, for example, human growth hormone, human protein C and clotting Factor VII, have been produced in host cells by transfecting these cells with DNA encoding these proteins and growing the recombinant cells under conditions favorable for the expression of the protein. Grinnell et al. describe the expression of recombinant human protein C (HPC) by human kidney cells in *Biotechnology*, 5:1189-1192 (1987). The proteins are secreted by the cells into the cell culture medium, and must be separated from the culture medium and the other components, such as cell waste products, cell debris and proteins or other material, which also has collected in the medium. In addition, the biological activity of the protein must be preserved, so the recovery conditions must be mild enough to preserve the biological activity of the protein, but, at the same time, thorough enough to effectively separate the protein from contaminants in the medium. Purity is often an important consideration, especially for pharmaceutical applications.

Recovery of proteins in biologically active form from cell culture medium presents a number of problems. For example, the desired protein must be separated from other closely related proteins in the cell culture medium, such as homologous, biologically inactive proteins, which may be associated with the protein. The recovery process should yield the biologically active form of the protein with a high level of purity.

Jones et al. describe a method for recovering refractile proteins (non-exported proteins which form insoluble protein granules within the host cell) from the cytoplasm of a host cell in U.S. Pat. No. 4,512,922. Related patents describing denaturing-refolding protein recovery systems include U.S. Pat. Nos. 4,599,197; 4,518,526; and 4,511,503.

Raush and Meng in U.S. Pat. No. 4,677,196 describe recovery of heterogenous proteins from a host cell, which are also in the form of refractile bodies.

Hung et al. in U.S. Pat. No. 4,734,362 describe a process for recovering recombinant refractile proteins from a host cell, involving denaturing the protein, and subsequent renaturing to yield the desired product.

The recovery and purification of human coagulation Factor VII is described by Brose and Majerus in *The Journal of Bioloqical Chemistry*, 255:1242-1247 (1980). They purified Factor VII from human plasma with a yield of about 30% using a process which involved first absorbing the proteins to barium citrate, and separating by chromatography.

Vitamin K-dependent proteins are a class of proteins involved in maintaining hemostasis. The dependency on vitamin K occurs during the biosynthesis of the proteins. Human protein C (HPC) is a vitamin K-dependent plasma glycoprotein that plays a key role in maintaining hemostasis. C. T. Esmon, *Science*, 235:1348-1352 (1987).

The binding of calcium ions ($Ca^{2+}$) to HPC causes a conformational change in HPC that can be measured by fluoresence emission spectroscopy. Johnson et al , *J. Biol. Chem.*, 258:5554-5560 (1983). The conformational change results in a change in surface charge distribution as measured by a difference in the migration pattern of the protein in an electrical field, such as agarose gel electrophoresis. Stenflo, J., *J. Biol. Chem.*, 251:355-363 (1976).

SUMMARY OF THE INVENTION

The invention provides a purification procedure by which an exported vitamin K-dependent protein produced by a host cell, or produced by a host cell after transformation or transfection with DNA encoding the protein, is recovered from the cell culture medium and purified. Vitamin K-dependent proteins bind divalent cations, such as calcium or barium ions, resulting in conformational changes in the protein, and alteration of the surface charges on the protein. These changes are utilized in the present process to control the binding affinity of the proteins to various substrates in the presence of divalent cations. The process uses conventional chromatography to separate the proteins based on the ionically altered binding affinity of the proteins.

In the present process, the cell culture medium containing the protein is treated with a chelating agent to remove endogenous divalent cations. The medium is contacted with an ion exchange resin, for which it has a strong affinity. The protein is then eluted from the resin with a solution containing divalent cations which bind to the protein which elutes as a protein-cation complex. The protein-cation complex is then contacted with a resin which has an immobilized chelating agent which binds the cation. The chelating resin preferentially binds the cation, and the protein alone elutes from this resin. The protein is then contacted with a second ion exchange resin for further purification. The protein is treated with a second cation-containing buffer forming a protein cation complex, and the complex is contacted with a hydrophobic resin. The protein-cation complex binds strongly to the hydrophobic resin. The protein bound resin can then be treated with a chelating agent which binds the cation, and highly pure protein can then be eluted from the hydrophobic resin. The binding differential between the protein and the protein-cation complex can be utilized to provide an efficient, non-denaturing process for recovering substantially pure, biologically active protein in yields of over 90% in each step.

DETAILED DESCRIPTION OF THE INVENTION

Figure 1:
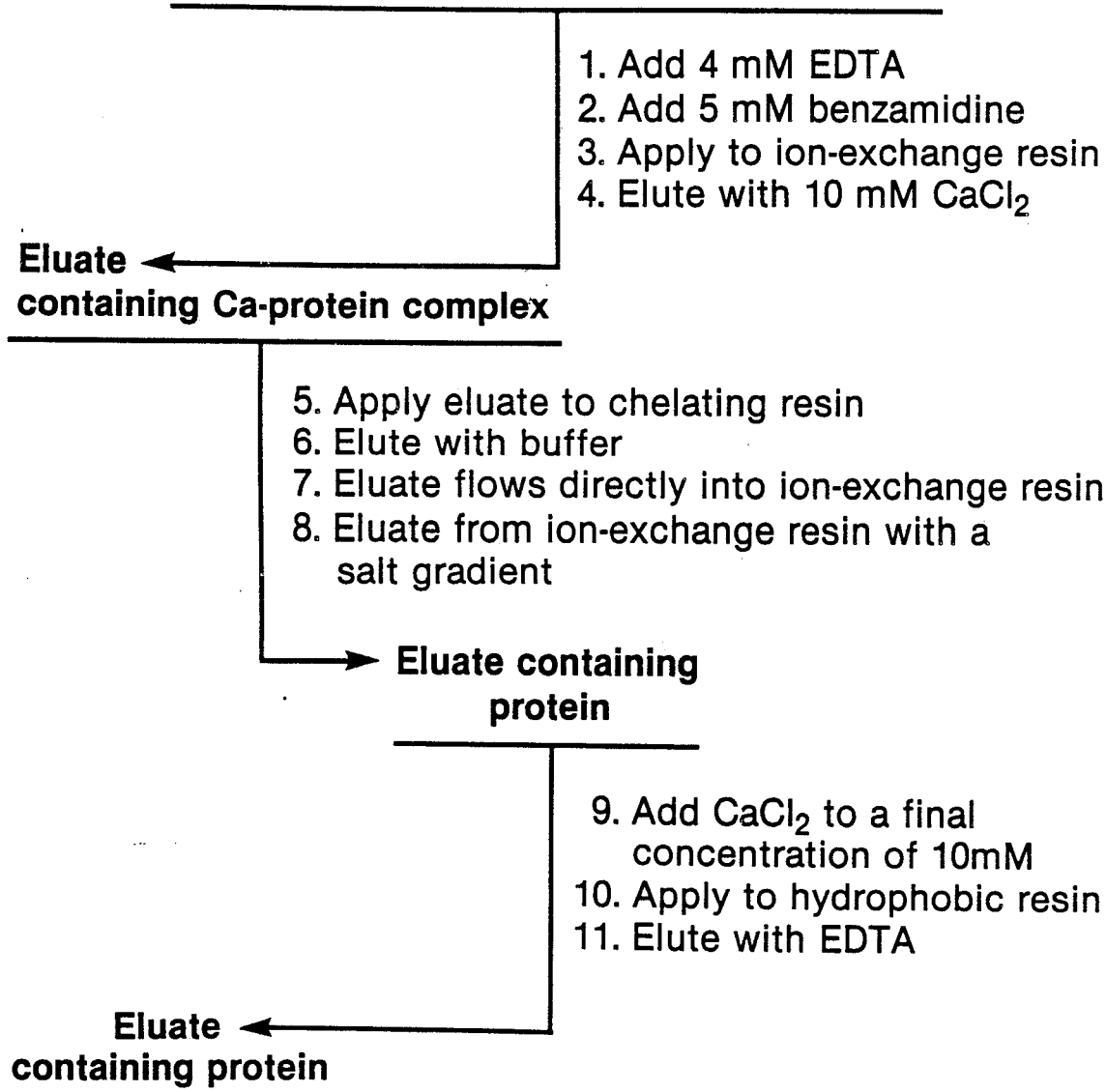
FIG. 1 shows a flow chart depicting the present process for purification of a divalent-cation binding protein.

HPC, and most of the other vitamin K-dependent proteins, bind divalent cations, such as $Ca^{2+}$. It is believed that the majority of binding sites on the proteins are modified glutamic acid residues. Ohlin et al., 1988, *J. Biol. Chem.*, 263:7411–7417. The reaction by which the glutamic acid residues are modified is gamma carboxylation, which is a post-translational modification performed by a microsomal enzyme vitamin K-dependent carboxylase. The gamma carboxylated glutamates (called Gla residues), are necessary for biological activity of vitamin K-dependent proteins. For example, in the case of HPC, the first nine consecutive glutamate residues in the HPC protein sequence must be modified by gamma carboxylation for the protein to be biologically active, (e.g., having antithrombotic activity).

For HPC, these Gla residues form most of the binding sites for $Ca^{2+}$. N. L. Esmon et al., *J. Biol. Chem.*, 258:5548–5553 (1983). There is a high-affinity $Ca^{2+}$ binding site that is formed between the epidermal growth factor-like domain in the light chain of HPC and the heavy chain of HPC as described by Johnson et al., in *J. Biol. Chem.*, 258:5554–5560 (1983); Ohlin and Stenflo, *J. Biol. Chem.*, 262:13798–13804 (1987); and Stearns et al., *J. Biol. Chem.*, 269:826–832 (1986). The change in surface charge distribution of the HPC protein is due to the neutralization of the nine Gla residues (2 negative changes per residue) by $Ca^{2+}$, resulting in a net loss of 18 negative charges. The change in surface charge distribution in HPC caused by $Ca^{2+}$ binding could also be a result of conformational changes. This change in conformation affects its binding profile to conventional resins such as those used in ion-exchange chromatography and hydrophobic chromatography. More particularly, this change causes conventional ion-exchange chromatography resins to behave like "pseudo-affinity" resins.

The method of the invention can selectively separate low specific activity protein from high specific activity protein. This selectivity is based on the number of Gla residues present on the protein. For example, low specific activity proteins, (i.e., proteins having fewer Gla residues), can be separated from higher specific activity proteins (i.e., proteins having a high number of Gla residues), based on the higher affinity of Gla-containing proteins for the resin. Proteins having a higher number of Gla residues will show more pronounced conformational and electrical changes upon complexing with a divalent cation such as calcium, and these high-activity proteins will therefore elute more readily from the column when an elution buffer containing divalent cations is used. This selectivity is extremely powerful and useful. Many mammalian cell lines are not capable of expressing fully biologically active, recombinant vitamin K-dependent proteins due to the lack of the presence of all the Gla residues. The method of the invention can separate the fully active vitamin K-dependent proteins from less active forms of the same protein. This procedure is simple, inexpensive, and readily set up by any biochemical laboratory.

The invention is based upon the use of conventional chromatography resins (such as ion-exchange or hydrophobic) as pseudo-affinity resins. The presence or absence of a low concentration of a divalent cation, specifically $Ca^{2+}$, affects the elution profile of HPC on conventional chromatography resins. This phenomenon can be extended to all vitamin K-dependent proteins and/or peptides, and potentially to all divalent cation-binding proteins, including $Ca^{2+}$-binding proteins, peptides or macromolecules. Since $Ca^{2+}$ is the physiologically most abundant effector divalent metal ion for binding to the known vitamin K-dependent proteins, it is being used for most of the subsequent experiments. However, other divalent cations such as strontium ($Sr^{2+}$), and barium ($Ba^{2+}$), can be substituted for $Ca^{2+}$. These metal ions achieve the same results.

The present process is effective for all vitamin K-dependent proteins, however produced, including, for example, human protein C (HPC), Factor IX, Factor X, Factor II, Factor VII, human protein S (HPS), Protein Z, bone Gla protein and bone matrix Gla protein. The present method is effective for both vitamin K-dependent protein zymogens, such as HPC, and for the corresponding activated forms of the serum proteases, such as activated Protein C (APC).

In one embodiment, the invention described herein is directed to procedures which are useful in isolating, purifying, reactivating and using heterologous recombinant proteins that, subsequent to expression in microorganisms (host cells), are secreted from the host cell into the cell culture medium. For purposes of the present invention, proteins which are secreted are referred to as "exported proteins". In another embodiment, the invention described herein is directed to the isolating, purifying, reactivating and using exported proteins that are produced in non-transformed cell lines.

When recombinant DNA technology is employed to induce host microorganisms to produce foreign proteins, such proteins are often referred to as "heterologous proteins" or "recombinant proteins". In the present invention, the term "protein" is meant to encompass all divalent cation binding polypeptides and proteins. The terms "heterologous" and "recombinant" are used interchangeably to denote a protein secreted by a host microorganism which binds a divalent cation.

GENERAL PROCEDURE

The protein is first cloned according to well-known standard recombinant DNA procedures. The cloning of HPC has been described by Beckmann et al. in *Nucleic Acids Research*, 13:5233 (1985). The expression of recombinant HPC (rHPC) with human kidney 293 cells has been described by Grinnell et al. in *Biotechnology*, 5:1189–1192 (1987).

The culture medium is collected and, optionally, centrifuged, at about 20,000 times gravity, for about twenty minutes at chill room temperatures (of about 4° C.) to remove cell debris. The supernatant contains the protein. After centrifugation, a protease inhibitor, such as benzamidine, and a chelating agent, such as EDTA or EGTA, in a concentration sufficient to remove all divalent cations, can be added to the medium (see FIG. 1, steps 1–2).

The medium can then be contacted with an ion exchange resin, such as an cationic quaternary or tertiary amine-based resin (FIG. 1, step 3). Some examples of available suitable commercial resins include Pharmacia Fast Flow Q (FFQ) and Mono Q, and QAE-A50-120 and DEAE tertiary/quaternary amine from Sigma. In one aspect of the invention, the resin can be contained in a column. However, the resin may also be in a bed or other configuration as long as the medium is able to filter through and contact a sufficient resin surface area to ensure adequate ion exchange. This step is carried out at chill-room temperatures (between 8°–10° C.).

The resin can be first equilibrated with a neutral pH buffer solution containing a small amount of protease inhibitor, chelating agent and, optionally, a monovalent salt. Any neutral buffer may be used, providing that it does not react with $Ca^{2+}$; for example, phosphate buffer forms an insoluble complex with $Ca^{2+}$, thus cannot be used. A preferred equilibrating buffer solution can contain about 20 mM Tris buffer, 2 mM EDTA, 2 mM benzamidine and 0.15 M NaCl, having a pH of about 7.4. The receptacle, (e.g., a column), can then be packed with the resin. Bed volume should be sufficient to provide binding sites for the protein. The culture medium, which has already been treated with a protease inhibitor and chelating agent, is then loaded onto the column. Flow rate is adjusted so that maximum protein binding occurs. In the case of HPC, the linear flow rate should be about 40–80 centimeters per hour.

The loaded column can then be washed with about three or more column volumes of a neutral buffer, (e.g., Tris buffer, pH 7.4), which contains a monovalent salt (e.g., NaCl or KCl), a protease inhibitor (e.g., benzamidine) and a chelating agent (e g., EDTA). Optionally, a second wash with about two column volumes of neutral buffer containing a salt and protease inhibitor can be done. At this point, the desired protein is bound tightly to the ionic resin, as these proteins have a high affinity for the resin. Most of the other proteins and contaminants in the cell culture medium have been washed away. To remove the protein from the column, an "elution" buffer containing the divalent cation, preferably calcium ($Ca^{2+}$), is used (FIG. 1, step 4). The calcium ions will bind preferentially to the protein forming a Ca-protein complex. This complex has a low affinity for the resin, therefore the Ca-protein-complex will be contained in the eluate. The elution buffer can be a combination of a neutral buffer (e.g., Tris), a monovalent salt (e.g., NaCl), a calcium salt (e.g., $CaCl_2$), and a protease inhibitor (e.g., benzamidine). A preferred elution buffer can contain 20 mM Tris, 0.15 NaCl, 10 mM $CaCl_2$ and 5 mM benzamidine, and have a pH of about 7.4. The protein elutes with the second column volume of the eluant. About ninety (90%) percent of the protein is eluted by the end of the second column volume. Protein recovery after this step is about 80–90%.

The eluate containing the protein can then be treated with a resin containing an immobilized chelating agent, and then contacted with a second ion-exchange resin (FIG. 1, steps 5–7). Columns or beds containing these two resins may, optionally, be set up in tandem, so that the eluate from the chelate column flows directly into the ion-exchange column. Alternatively, the eluate from the chelating column can be collected, and then loaded onto the ion-exchange column. A commercial chelating column containing a resin having an immobilized chelating agent can be used, such as Chelex 100 (Biorad), which has immobilized EDTA. The purpose of this column is to remove the calcium from the protein. The ion-exchange resin can be the same type as the ion-exchange resin used in the first step. In this step, both resins are first equilibrated by washing with a neutral pH buffer, (e.g., Tris buffer) containing a low concentration of salt. The capacity of the columns is dependent upon the sample volume. Bed volume of the chelating column should preferably be about 20 ml for each 200 ml of sample; and bed volume for the ion-exchange column should preferably be about 50 ml for each 0.5–1.0 grams of protein. Both columns should be run at a flow rate sufficient to remove unbound calcium, and further purify the protein. This step can also be carried out at chill room temperatures. In a preferred method, the eluate from the first step is loaded on the tandem-linked columns. The loaded chelate column can then be washed with two column volumes, based on the chelate-column volume, of a neutral pH buffer having a low concentration of salt. Once the liquid has eluted, the chelate column can then be disconnected. At this point, the protein is bound to the ion exchange column. It has been found that the protein will bind to the ion exchange column at low salt concentrations, and elute at higher salt concentrations. To elute the protein, therefore, the column can be treated with a series of buffers containing a salt gradient (see FIG. 1, step 8 and FIG. 2). For example, a buffer, consisting of pH 7.4 Tris buffer and 1 M NaCl, can be contacted with the column using a series of solutions containing between 0–50% of this buffer over about twenty column volumes. The protein begins to elute with the solution containing about 27% buffer, and peaks at about 30% buffer. The protein may also be eluted using high salt buffers in lieu of a gradient (e.g., about 0.4 to 1 M NaCl). The elution is monitored by measuring the change in optical density using spectroscopy to measure absorbance at 280 mm as described by Kisiel and Davie in *Meth. in Enzymology*, 80:320–332 (1981). At this point, the protein recovery is more than 90%.

The protein-containing eluate fractions are then contacted with a hydrophobic resin in order to concentrate and purify the protein by removing protein contaminants from the eluate. A hydrophobic resin, such as phenyl superose, can be used. Commercially available resins include phenyl superose HR5/5 and phenylsepharose CL-4B, both from Pharmacia. The hydrophobic resin can first be equilibrated with a neutral buffer containing, optionally, a monovalent salt, and a divalent cation. A preferred equilibration buffer is 20 mM Tris, 1 M NaCl, and 10 mM $CaCl_2$, having a pH of about 7.4.

In this step, the protein containing fraction, eluted from the prior step, is treated with a second divalent cation, such as a buffer containing about 10 mM $CaCl_2$, and loaded onto the hydrophobic resin and washed with the equilibration buffer (FIG. 1, steps 9–10). It has been found that vitamin K-dependent proteins bind weakly to hydrophobic resins, such as phenyl-superose; in the absence of $Ca^{2+}$; but have a high affinity for the resin in the presence of $Ca^{2+}$, and can thus be eluted from the resin with a solution containing a chelating agent, such as EDTA. The protein can be eluted with an elution buffer containing a neutral buffer, a low concentration of monovalent salt, and a chelating agent. A preferred elution buffer can contain about 20 mM Tris, 0.15 M NaCl and 1 mM EDTA (pH 7.4).

The purity of the protein using this procedure is greater than 98%, as determined by SDS:PAGE chromatography. Laemmli, *Nature*, 227:680–685 (1974). The protein also retains 100% biological activity as determined by functional assays, as described by Grinnell et al., in *Biotechnology*, 5:1189–1192 (1987).

The invention is further illustrated by the following exemplification.

EXEMPLIFICATION

Example 1

Separation of HPC using Anion-exchange column chromatography

A quaternary amine-based strong anion exchange resin (i.e., Fast Flow Q or Mono-Q from Pharmacia) was used for the following experiments. Quaternary amine based resin from any reputable commercial company should service (e.g., QAE-A50-120 from Sigma).

HPC binds also to tertiary amine based resins, such as DEAE-sepharose CL-6B (Sigma). These resins can also be used to obtain the same results.

The results illustrate that HPC binds to the anion exchange resin in the absence of $Ca^{2+}$.

Materials

Figure 2:
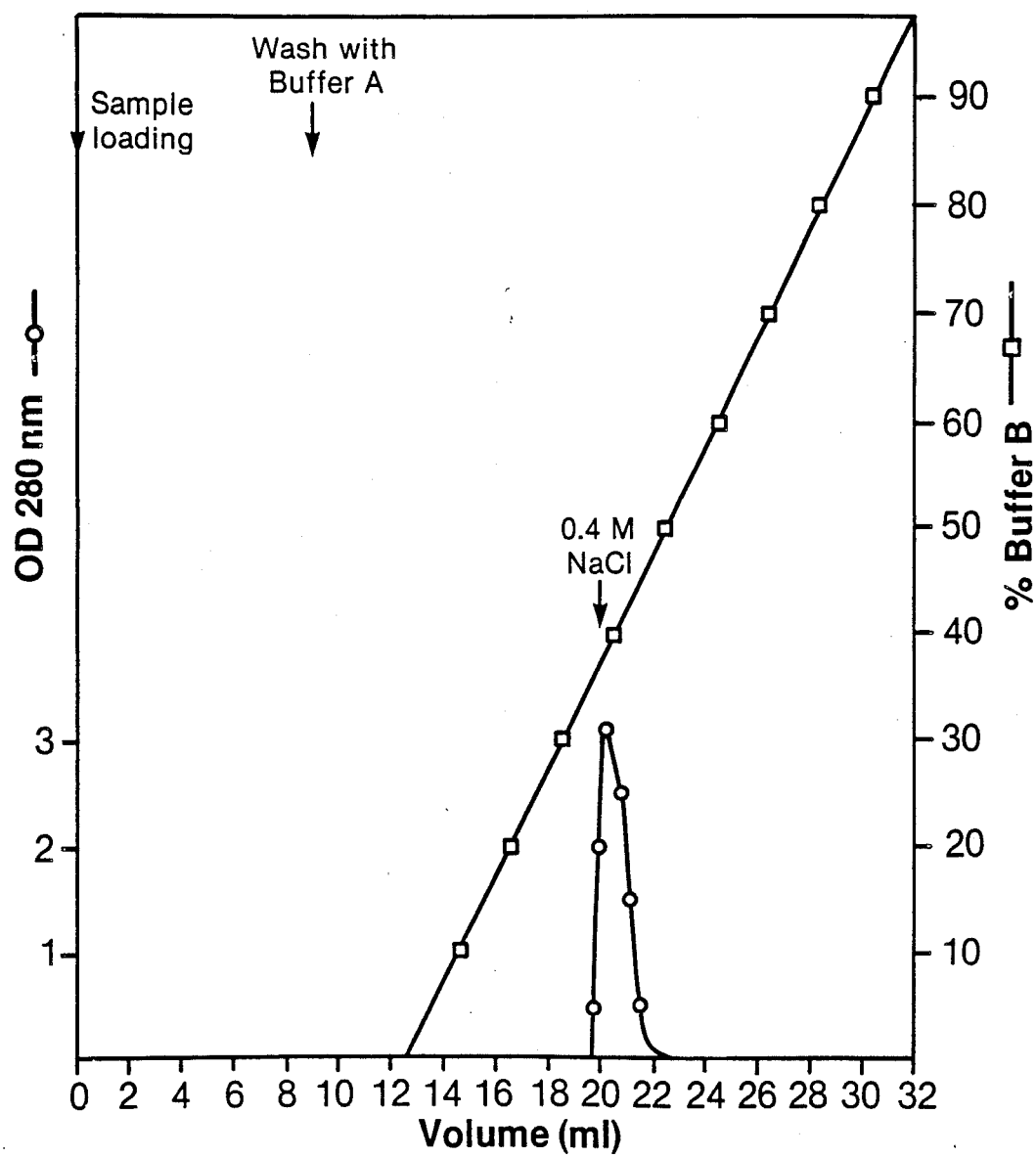
FIG. 2 shows the elution profile of human Protein C from a Pharmacia MonoQ ion exchange resin using a NaCl gradient.

Column: Pharmacia Mono-Q, HR5/5
Instrument: Pharmacia FPLC LCC-500 system to run the NaCl gradient
Buffer A: 20 mM Tris, pH 7.4, 0.15 M NaCl
Buffer B: 20 mM Tris, pH 7.4, 1M NaCl
Flow rate: 1 ml/min
NaCl gradient 0–100% Buffer B in 20 minutes The column was conditioned as suggested by the manufacturer. Then the column (bed volume 1 ml) was equilibrated with Buffer A. A sample containing 6 mg of plasma HPC in 8.5 ml of Buffer A was loaded onto the column, and the column was washed with three column volumes (3 ml) of Buffer A prior to the start of the NaCl gradient. As shown in FIG. 2, all of the HPC bound to the resin. The concentration of HPC was monitored by optical density by measuring absorbance at 280 nm as described by Kisiel and Davie in *Meth. in Enzymology*, 80:320–332 (1981).

It was found that if HPC is in Buffer A containing 2 mM $CaCl_2$, the HPC would not bind to the Mono-Q column. 2 mM $CaCl_2$ is what is typically present in cell culture media or in human plasma. HPC was shown to elute from Mono-Q resin with a solution containing 0.4 M NaCl in 20 mM Tris, (pH 7.4). The amount of NaCl needed to elute HPC is pH dependent. For example, the lower the pH, the higher is the concentration of NaCl required and the higher the pH, the lower the concentration of NaCl required.

Example 2

Elution of HPC from an anion exchange column with a low concentration of $CaCl_2$ The following experiment uses the Pharmacia Mono-Q column and the same protocol described in Example 1.

Materials

Figure 3:
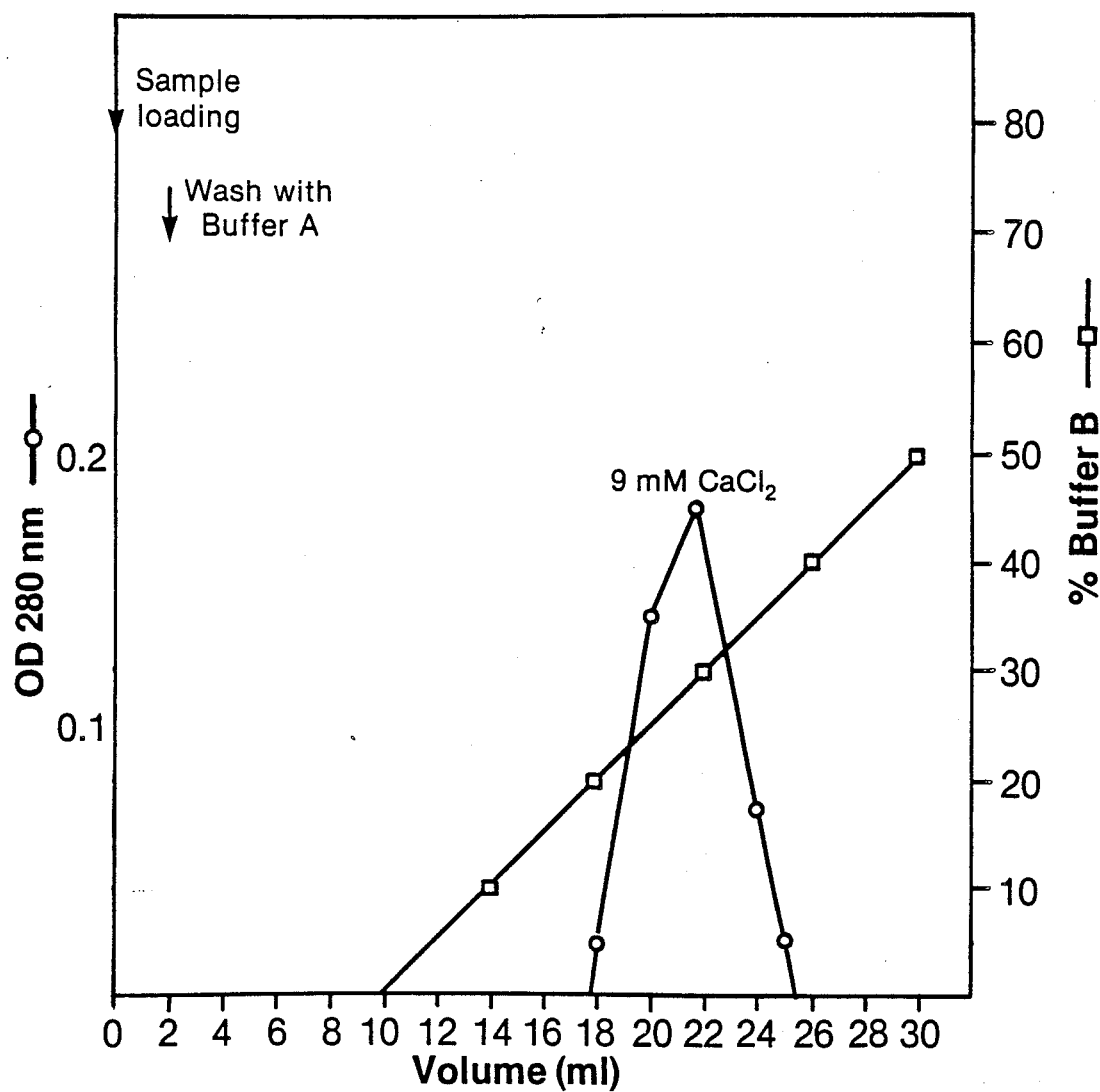
FIG. 3 shows the elution profile of human Protein C from a Pharmacia MonoQ ion exchange resin using a $CaCl_2$ gradient.

Column: Pharmacia Mono-Q HR 5/5
Instrument: Pharmacia FPLC LCC 500
Buffer A: 20 mM Tris, pH 7.4, 0.15 M NaCl
Buffer B: 20 mM Tris, pH 7.4, 0.15 M NaCl, 30 mM $CaCl_2$
Flow rate: 1 ml/min
NaCl Gradient: 0–50% buffer B in 2 minutes The column was equilibrated with Buffer A. A sample containing 0.6 mg of HPC dissolved in 0.7 ml of Buffer A was loaded onto the column with Buffer A prior to the development of the $Ca^{2+}$ gradient. The HPC was eluded with a gradient of 6–9 mM $CaCl_2$ in 20 mM Tris pH 7.4, 0.15 NaCl. The results, shown in FIG. 3, show that HPC elutes with increasing concentrations of $CaCl_2$.

HPC was quantified by determining optical density by measuring absorbance at 280 nm as described by Kisiel and Davies in *Meth. in Enzymology*, 80:320–332 (1981).

Example 3

Specificity of divalent metal cations for the elution of HPC from an anion exchange column The experiment was set up and run as described in Example 2. It was shown that HPC can be eluted isocratically with various concentrations of $CaCl_2$ in buffer.

Buffer A: 20 mM Tris, pH 7.4, 0.15 M NaCl
Buffer C: 20mM Tris, pH 7.4

The results are shown in Table 1.

TABLE I

| divalent cation | Buffer A | Buffer C | Yield of HPC |
|---|---|---|---|
| 5 mM $CaCl_2$ | + | − | 80% |
| 10 mM $CaCl_2$ | + | − | 95% |
| 10 mM $CaCl_2$ | − | + | 0% |
| 10 mM $MgCl_2$ | + | − | 20% |

The data indicated that the divalent cation effect of $Ca^{2+}$ in eluting HPC is ion-specific because magnesium chloride ($MgCl_2$) in the same concentration is much less effective than $CaCl_2$.

The ionic strength of the buffer containing the $CaCl_2$ is also important. In the absence of 0.15 M NaCl, $CaCl_2$ at 10 mM $CaCl_2$ was ineffective in eluting HPC from Mono-Q column.

Example 4

Selectiveness of using 10 mM $CaCl_2$ to elute HPC instead of 0.4 M NaCl from a Mono-Q column Two percent fetal calf serum (FCS) conditioned media from human kidney 293 cells (Grinnell et al., (1987) *Biotechnology*, 5:1189–1192) expressing 3.3 μg/ml of rHPC was used to show the achievement of 240 fold purification in one step using an anion exchange column.

Figure 4:
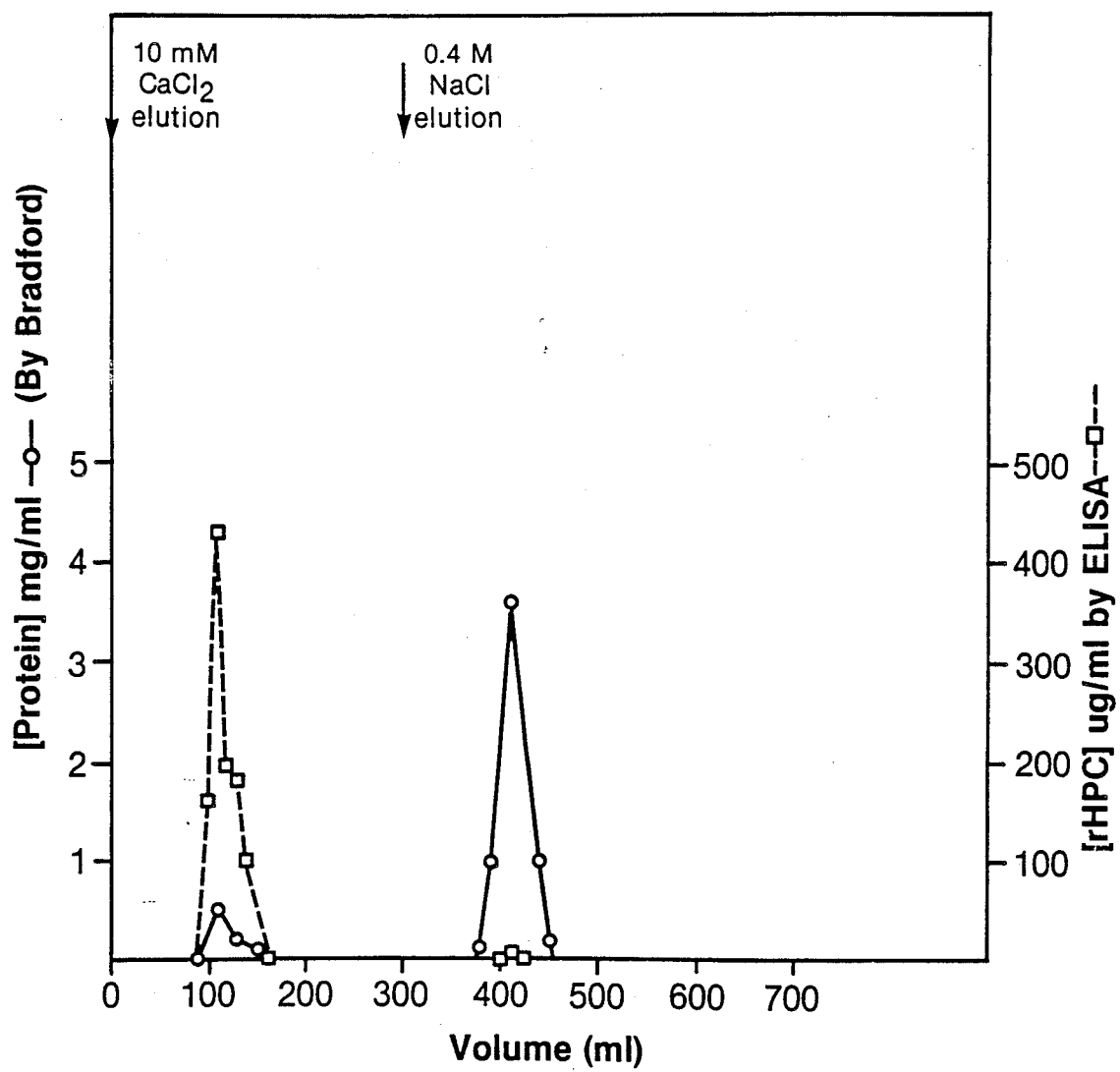
FIG. 4 shows the elution profiles of human Protein C from a Pharmacia Fast Flow Q ion exchange resin using both a $CaCl_2$ elution buffer and a high NaCl buffer.

100ml of Pharmacia Fast Flow Q (FFQ) resin was properly prepared as recommended by the manufacturer. The FFQ resin was then equilibrated with a buffer solution containing 20 mM Tris, 0.15 M NaCl, 2 mM EDTA, 2 mM benzamidine, (pH 7.4). EDTA and benzamidine were added to the 3.3 liters of 2% FCS conditioned media containing 3.3 μg/ml of rHPC to a final concentration of 4 mM and 5 mM respectively. Then the culture media was passed through the FFQ column (3×16 cm) at a linear flow rate of 20cm.h$^{-1}$. The column was washed first with 300 ml (3 column volumes) of a solution containing 20 mM Tris, 0.15 M NaCl, 2 mM EDTA, 2 mM benzamidine (pH 7.4), then 300 ml (3 column volumes) of a solution containing 20 mM Tris, 0.15 M NaCl, 2 mM benzamidine (pH 7.4) then 300 ml of a solution containing 20 mM Tris, 0.15 M NaCl, 2 mM benzamidine, 10 mM $CaCl_2$ (pH 7.4). The column was then further eluted with a solution containing 20 mM Tris, 0.4 M NaCl, 2 mM benzamidine (pH 7.4). The amount of HPC was determined by measuring $OD_{280}$ as described in Example 2. Specific activity of HPC was determined according to the procedure described by et al in *Biotechnology*, 5:1189–1192 (1987), as follows: HPC was first activated with an immobilized thrombomodulin-thrombin complex (obtained from Dr. C. T. Esmon, Oklahoma Medical Research Foundation). The amidolytic activity of the activated protein C (APC) was measured by the hydrolysis of a tripeptide substrate S-2238 (Helena). The anticoagulant activity of HPC was determined by the prolongation of an activated partial thromboplastin time (APTT) using reagents from Helena. The assays and the definition of a unit of the specific activity of HPC is that described by Grinnell et al. The results are shown in FIG. 4, and below in Table II.

TABLE II

| Sample | Total protein (mg) | Total rHPC (mg) | Purity of rHPC [HPC] antigen | Specific activity (units/mg HPC) |
|---|---|---|---|---|
| starting media | 4422 | 10.9 | 0.25% | 0.074 |
| unbound fraction | 4290 | 0.016 | 0.0004% | — |
| 10 mM CaCl$_2$ fraction | 16.2 | 9.4 | 58% | 17.5 |
| 0.4M NaCl fraction | 115.2 | 0.12 | 0.1% | — |

The results from this experiment clearly demonstrated that the purity of rHPC was increased from 0.25% in the starting material to about 58% (a total increase of 232 fold). By comparison, using the "conventional" mode of eluting rHPC with 0.4 M NaCl, the purity of rHPC at that stage is only 7% (a total increase of 28 fold). So the present mode gave an additional 8.3 fold of purification.

Example 5

The elution of proteins from anion exchange chromatography is specific for binding proteins and vitamin K-dependent proteins.

Two non-Ca$^{2+}$ binding and non-vitamin K-dependent proteins were used in this example. Both proteins normally bind to the Pharmacia Mono-Q column under the conditions specified in Example 1, i.e. 20 mM Tris, 0.15 M NaCl (pH 7.4). The two proteins used were glucose oxidase and amyloglucosidase (*Aspergillus niger* Cat. # G2133 and A3423, respectively, from Sigma). The experiments described in Examples 1 and 2 were repeated for each of the two proteins and the results are shown in Table III.

TABLE III

| protein | Concentration of CaCl$_2$ required for elution in 20 mM Tris, 0.15M NaCl (pH 7.4) | Concentration of NaCl required for elution in 20 mM Tris (pH 7.4) |
|---|---|---|
| glucose oxidase | 18 mM | 0.30M |
| amyloglucosidase | over 20 mM | 0.36M |
| HPC | 9 mM | 0.40M |

Example 6

Selectivity of the "pseudo-affinity" mode for removal of non-protein contaminants Conditioned culture media from human kidney 293 cells expressing rHPC was used for this experiment. Grinnell et al., *Biotechnology*, 5:1189–1192 (1987). The culture media contained endotoxin (lipopolysaccharide A) at 80 endotoxin units/ml (8 ng endotoxin/ml). Endotoxins are heterogeneous molecules of lipopolysaccharide, negatively charged, and derived from the outer coat of gram-negative bacteria. The experiment was carried out as described in Example 4, except that the endotoxin level was measured in place of total protein concentration. Endotoxin levels were measured using an Endotoxin assay kit from Whittaker Bioproducts. Starting with a total of $4 \times 10^6$ endotoxin units, $5.7 \times 10^4$ endotoxin units were recovered in the rHPC peak eluted with 10 mM CaCl$_2$, 20 mM Tris, 0.15 M NaCl, pH 7.4. This represents a total removal of 98.5% of the endotoxin from the starting culture media after one step of purification.

Example 7

Selectivity of the "pseudo-affinity" mode for the removal of contaminating organisms The experiment was carried out as described in Example 6. $5 \times 10^{10}$ phi-X174 phages (ATCC number 13706-sinshiemer-c-bl) were introduced into conditioned culture media from human kidney 293 cells expressing rHPC. This media was then passed through the FFQ column. Only $1 \times 10^5$ phi-X174 phages were recovered in the CaCl$_2$ eluted fraction containing the rHPC, while $2-3 \times 10^6$ phi-X174 phages were recovered in the 0.4 M NaCl eluted fraction. These show that the CaCl$_2$ elution ("pseudo-affinity" mode) gives 20–30 fold better selectivity than the 0.4 M NaCl elution (conventional mode).

Example 8

Purification of recombinant Human Protein S (HPS).

A. Purification of rHPS produced by AV12 Cells

HPS is a vitamin K-dependent protein containing 11 Gla residues. Conditioned culture media containing HPS was obtained by conventionally transforming Syrian hamster AV12 cells (ATCC number CRL 9595) with plasmid pShD, constructed in substantial accordance with the teaching of United States patent application Ser. No. 866,662, filed May 27, 1986, Attorney Docket Number X-6922 and incorporated by reference herein, and was used for the following experiments.

The procedure described in Example 1 was repeated using the present culture media containing rHPS. rHPS was eluted using the "conventional" mode (described in Example 7) from a Pharmacia FFQ column with a solution of 20 mM Tris, 0.33 M NaCl, (pH 7.4). The CaCl$_2$ elution procedure described in Example 2 was then used for the culture media containing rHPS. rHPS was eluted successfully using the "pseudo-affinity" mode from the FFQ column with a solution of 20 mM Tris, 0.15 M NaCl, 3.5 mM CaCl$_2$ (pH 7.4).

B. Purification of high specific activity rHPS produced by 293 cells rHPS was also obtained by conventionally transforming human kidney 293 cells with plasmid pShD, then culturing the cells in serum-free media. The rHPS culture media was added to Pharmacia Fast Flow Q resin then washed with Buffer A in substantial accordance with the teaching of Example 1. The CaCl$_2$ elution procedure described in Example 2 was then used for the HPS culture media, except that the elution buffer contained 20 mM Tris, 0.15 M NaCl, 3.0 mM CaCl$_2$ (pH 7.4). About three column volumes were collected, then the column was eluted with a buffer containing 20 mM Tris, pH 7.4, 0.5 M NaCl. The biological activity of the eluted rHPS from both elution buffers was then tested using the assay method of Malm, et al (1987) *Eur. J. Biochem.* 165:39–45, the entire teaching of which is herein incorporated by reference.

rHPS obtained from AV12-transformed cells grown in serum-free media (as in Example 8A) was also loaded onto Pharmacia Fast Flow Q resin. The AV12-derived rHPS was then eluted using 3.0 mM $CaCl_2$, followed by a 0.5 M NaCl elution, substantially as described above for the 293-derived rHPS. Bioactivities were then assayed by the method of Malm et al.

Ninety-seven (97%) of the total functional activity of the 293-derived rHPS was eluted with a solution of 20 mM Tris, 0.15 M NaCl, 3.0 mM $CaCl_2$, (pH 7.4) ($CaCl_2$ fraction), while the remaining three (3%) percent of the functional activity of the 293-derived rHPS was eluted with a solution of 20 mM Tris 0.5 M NaCl (pH 7.4), (NaCl fraction). However, only forty-three (43%) percent of the total functional activity of the AV12-derived rHPS was eluted in the $CaCl_2$ fraction, while fifty-three (53%) percent of the functional activity of the AV12-derived rHPS was eluted in the NaCl fraction.

The Gla content and beta-hydroxyaspartate content were measured in both the $CaCl_2$ and NaCl fractions of rHPS as described in Example 9. The rHPS molecules from the $CaCl_2$ and NaCl fractions displayed no differences in beta-hydroxyaspartate content, molecular weight (reduced and non-reduced SDS-PAGE) and N-terminal protein sequence. However, the rHPS molecules from the two fractions did differ in Gla content, as the molecule from the NaCl fraction has 2 fewer Gla residues than does the molecule from the $CaCl_2$ fraction. This accounts for the lower specific activity (about 50% less) of rHPS derived from AV12 cells as compared to fully functional rHPS derived from 293 cells.

This experiment demonstrated that the "pseudo-affinity" mode ($CaCl_2$ fraction) of eluting rHPS using anion exchange chromatography can selectively separate low specific activity rHPS (low Gla content) from high specific activity rHPS (high Gla content).

Example 9 rHPC with a high specific activity can be separated from low specific activity rHPC.

Human Prothrombin protein has 10 Gla residues, which are essential for biological activity. Borowski et al., *J. Biol. Chem.*, 260:9258-9264 (1985). Natural variants of human Prothrombin missing two or four Gla residues retain only 66% and 5% of their biological activity, respectively. Since prothrombin missing 2 Gla out of a total of 10 Gla results in a drop of more than 30% of activity, the presence of all Gla residues are essential for full activity.

rHPC that was only partially active (30–60% anticoagulant activity as compared to a plasma HPC standard) when measured in the crude culture media was obtained by transforming Syrian hamster AV12 cells (ATCC number CRL 9595) with plasmid p4-14, constructed in substantial accordance with the teaching of United States patent application Ser. No. 129,028, filed Dec. 4, 1987, Attorney Docket Number X-6606A and incorporated by reference herein. Activity was measured as described for HPC in Example 4. The rHPC from this culture media was absorbed and eluted according to the procedure described in Example 4.

Forty-five (45%) percent of the total starting rHPC in the culture media was eluted with a solution of 20 mM Tris, 0.15 M NaCl, 10 mM $CaCl_2$, (pH 7.4) ($CaCl_2$ fraction), and 20% was eluted with 20 mM Tris, 0.4 M NaCl, (pH 7.4) (NaCl fraction). The anticoagulant activity of the rHPC in the $CaCl_2$ fraction and in the NaCl fraction, were 100% and 25% respectively, as compared to a plasma HPC standard. The Gla content and beta-hydroxyaspartate content were measured in the rHPC in both the $CaCl_2$ fraction and in the NaCl fraction, using a procedure adapted from the procedure described by Kuwanda and Katayama in *Anal. Biochem.*, 131:173-179 (1983): the alkaline hydrolysis of the protein prior to the amino acid analysis was carried out with a teflon vial with miniert valves. (Pierce, Cat. #14005,10130). The protein sample in 2.5N NaOH was evacuated and purged with $N_2$ via the miniert valve using a Waters picotag work station. After 20 hours of hydrolysis at 110° C., the hydrolysate was neutralized, extracted and derivatized with o-phthalaldehyde/e-thanethiol as described by Kuwada and Katayama. The HPLC analysis was carried out under the following conditions:

column: Nucleosil 5SB (4.6×50) (Macherey-Nagel)
Isocratic elution: 20 mM Na citrate, pH 4.30 in 50% acetylnitrile
Flow rate: 1.5 ml/minute.
The following elution times were obtained:

| AMINO ACIDS | ELUTION TIME |
| --- | --- |
| non-acidic amino acids | 6 min |
| Glu | 9.5 min |
| Asp | 13 min |
| erythyro-beta-OH-asp | 20 min |
| threo-beta-OH-asp | 34 min |
| Gla | 44 min |
| cysteic acid | 53 min |

The $CaCl_2$ fraction and the NaCl fraction were found to contain 9 and 6.5 moles of Gla per mole of rHPC, respectively.

The number of Gla residues present correlates very well with biological activity in rHPC as predicted by what was reported in the literature for other vitamin K-dependent proteins. Borowski et al., *J. Biol. Chem.*, 260:9258-9264 (1985). Other than the difference in Gla content in the rHPC between the $CaCl_2$ fraction and the NaCl fraction, no other difference was detected in beta-hydroxyaspartate content, molecular weights (reduced and non-reduced SDS-PAGE) and N-terminal protein sequence. N-terminal protein sequence analysis was performed by automated Edman degradation chemistry on Applied Biosystem model 470A gas phase sequenator with on-line HPLC system (model 120A) for the analysis of PTH-amino acids.

This experiment demonstrated that the "pseudo-affinity" mode ($CaCl_2$ fraction) of eluting rHPC using anion exchange column chromatography can selectively separate low specific activity rHPC (low Gla content) from high specific activity rHPC (high Gla content).

Example 10

Elution of (APC) from an anion exchange column

HPC is the zymogen form of the active serine protease, activated human Protein C (APC). The only molecular difference between HPC and APC is that APC lacks a 12-amino acid peptide at the N-terminus of the heavy chain of the HPC. Thus, there is no difference in the Gla content of APC and HPC.

rAPC was prepared from rHPC with immobilized thrombomodulin-thrombin complex as described by Grinnell et al. *in Biotechnology*, 5:1189-1192 (1987). The experimental protocol described in Examples 1 and 2 were repeated for rAPC. The results of the elution profiles of rAPC from a Pharmacia Mono-Q column were identical to that of rHPC. The amount of $CaCl_2$ or NaCl required for elution of rAPC for either the "pseudo-affinity" mode or the "conventional" mode were identical to that of rHPC.

Example 11

-Hydrophobic column chromatography

Three of the most common conventional types of column chromatographies used in biochemical research are ion-exchange, hydrophobic/reverse phase and size-exclusion. The former two types are dependent on the surface charge distributions of the biochemical compounds of interest, while size-exclusion chromatography is not. Hydrophobic column chromatography was therefore used to illustrate that the "pseudo-affinity" vitamin K-dependent proteins can be separated on this type of column using the "pseudo-affinity" mode.

Hydrophobic side chains are linked to a rigid support to create hydrophobic column resins. Phenyl groups were used for this illustration. Other hydrophobic side chains, such as various lengths of aliphatic hydrocarbons, can also be used. Two different types of rigid supports were used for phenyl superose HR 5/5 and phenyl sepharose CL-4B, both from Pharmacia.

(a) Materials:

Column : Pharmacia phenyl superose HR 5/5
Buffer A: 20 mM Tris, 2 M NaCl, pH 7.4
Buffer B: 20 mM Tris, 0.15 M NaCl, pH 7.4
Buffer C: 20 mM Tris, 2 M NaCl, 10 mM $CaCl_2$, pH 7.4
Buffer D: 20 mM Tris, 0.15 M NaCl, 10 mM $CaCl_2$, pH 7.4
Flow rate: 0.5 ml/min.
Chromatography system: Pharmacia FPLC LCC-500 system The column was prepared as suggested by the manufacturer and then equilibrated with buffer A. 1 mg of rHPC was dissolved in buffer A, and then applied to the column. The concentration of protein was monitored by measuring the optical density at 280 nm. The rHPC did not bind to the column. No further material could be eluted with a gradient of 0-100% buffer B in 40 minutes. rHPC was dissolved in buffer C and then applied to the column. All the rHPC bound to the phenyl superose column. The only difference between buffer A and C is that buffer C contained 10 mM $CaCl_2$. A gradient of 0-100% buffer D was developed over 40 minutes. rHPC was eluted at 60% bufffer D and 40% buffer C, or at 20 mM Tris, 0.9 M NaCl, 10 mM $CaCl_2$, (pH 7.4).

Thus, it was shown rHPC has a higher affinity to hydrophobic resins in the presence of a low concentration of $Ca^{2+}$.

The experiment was repeated using a phenyl sepharose column:

(b) Materials column: Pharmacia phenyl sepharose CL-4B 0.5×5 cm
flow rate: 0.5 ml/min
rHPC was shown to bind 100% to the column either with buffer A (20 mM Tris, 2 M NaCl, pH 7.4) or with a solution of 20 mM Tris, 1 M NaCl, 10 mM $CaCl_2$, (pH 7.4). However, rHPC would not bind to the column in a solution of 20 mM Tris, 1 M NaCl, pH 7.4.

Example 12

Using "pseudo-affinity" chromatography to purify rHPC from cell culture media

The following scheme is an example of a purification scheme for a certain set of conditions and variables.

All the following steps were carried out at chill room temperature (8°-10° C.).

Step 1. Anion-exchange Fast Flow Q column

Serum free conditioned culture media from 293 cells expressing rHPC at 5 μg/ml was used. The serum free culture media contained protein/peptide supplements of insulin and transferring. The concentration of rHPC generally comprised 10-15% of the total protein in the conditioned culture media. Pharmacia Fast Flow Q resin (FFQ) was cleaned with 1N HCl and 1N NaOH in a manner suggested by the manufacturer. The resin was then packed into a 10×20 cm column. For every 500 liters of culture media, 1 liter of FFQ resin was needed. The column was packed to flow at a rate of 120 cm.h$^{-1}$ with 20 mM Tris, 1 M NaCl, (pH 7.4). The column was equilibrated with a solution of 20 mM Tris, 0.15 M NaCl, 2 mM EDTA, 2 mM benzamidine, (pH 7.4).

Solutions of 0.2 M EDTA, (pH 7.4) and 1 M benzamidine were added to the culture media containing rHPC to a final concentration of 4 mM and 5 mM, respectively. The culture media was then applied to the FFQ column at a flow rate of 80 cm.h$^{-1}$.

The FFQ column was then washed with a minimum 3 column volumes of a solution containing 20 mM Tris, 0.15 M NaCl, 2 mM EDTA, 5 mM benzamidine, (pH 7.4). The FFQ column was then further washed with a minimum 3 column volumes of a solution containing 20 mM Tris, 0.15 M NaCl, 5 mM benzamidine, (pH 7.4). The rHPC was eluted with a solution of 20 mM Tris, 0.15 M NaCl, 10 mM $CaCl_2$, 5 mM benzamidine, (pH 7.4). The flow rate was 5 cm.h$^{-1}$. The rHPC was detected with Bradford protein reagent (M. Bradford, (1976) *Anal. Biochem.*, 72:248-254) or ELISA assay as described by Grinnell et al., *Biotechnology*, 5:1189-1192 (1987). The rHPC eluted at the beginning of the second column volume using this elution buffer. Ninety (90%) percent of rHPC was eluted in half a column volume.

Step 2 Chelex 100 column in tandem with Fast Flow Q column.

A Chelex 100 column (Bio-rad) was used to remove the $Ca^{2+}$ in the rHPC from step 1. The FFQ was run in the conventional mode in this step. Chelex 100 resin (300 ml) was washed with 1 N NaOH —$H_2O$—1 N HCl —$H_2O$ as recommended by the manufacturer. The resin was packed into a 3.2×40 cm column and was washed with a solution of 1 M Tris, (pH 7.4). The column was equilibrated with an equilibration buffer containing 20 mM Tris, 0.15 M NaCl, (pH 7.4). The 1 M Tris wash was necessary to achieve fast equilibration of the Chelex 100 to pH 7.4. The FFQ column (3.2×25 cm) was cleaned as described in Step 1, and equilibrated with a solution of 20 mM Tris, 0.15 M NaCl, (pH 7.4). The Chelex 100 column was hooked up in tandem with the FFQ column such that the eluate containing rHPC from Step 1 will pass through the Chelex 100 first, and then the FFQ.

After all of the rHPC from Step 1 had been loaded, the columns were washed with 1.5 liters of the equilibration buffer. Then the Chelex 100 column was unhooked from the FFQ.

The FFQ was further washed with 600 ml of the equilibrating buffer. The FFQ was then washed with 600 ml of a solution of 20 mM Tris, 0.25 M NaCl, (pH 7.4). No rHPC was eluted here. The rHPC was eluted from the FFQ with a high salt solution of 20 mM Tris, 0.4 M NaCl, (pH 7.4). The rHPC was detected by monitoring absorbance at 280 nm. The yield of rHPC from this step was 90–95%.

Step 3. Hydrophobic phenyl-sepharose resin

A 3.2×40 cm column of phenyl-sepharose CL-4B (Pharmacia) was packed and then washed with 3 column volumes each of the following solutions at a flow of 20 cm.h$^{-1}$:50% methanol; $H_2O$; 1% acetic acid; $H_2O$; 0.1 M NaOH; $H_2O$.

The column was then equilibrated with an equilibration buffer containing 20 mM Tris, 1 M NaCl, 10 10 mM $CaCl_2$, (pH 7.4). The rHPC from Step 2 was diluted with an equal volume of a solution containing 20 mM Tris, 2 M NaCl, 20 mM $CaCl_2$, (pH 7.4), and put through the column.

The column was further washed with 1 liter of equilibration buffer. The rHPC was eluted with a solution of 20 mM Tris, 0.15 M NaCl, 1 mM EDTA, (pH 7.4).

The recovery of rHPC at this step was about 85%. The purity is greater than 98% as measured by SDS-PAGE (Laemmli, (1974) *Nature*, 227:680–685) or specific activity as described in Example 4. The level of endotoxin was reduced 10 fold after this step.

Equivalents

Those skilled in the art will recognize, or be able to ascertain, using no more than routine experimentation, numerous equivalents to the specific substances and procedures described herein. Such equivalents are considered to be within the scope of this invention, and are covered by the following claims.

I claim:

1. A method for recovering and purifying vitamin K-dependent proteins from a cell culture medium of transformed cells which produce recombinant vitamin K-dependent proteins, comprising:
   (a) removing divalent cations from the medium;
   (b) contacting the medium with a protein-binding anion-exchange resin under conditions such that the protein is bound to the resin;
   (c) treating the resin-bound protein with a divalent cation under conditions appropriate to form a cation-protein complex and to thereby dissociate the protein from the resin; and
   (d) treating the cation-protein complex under conditions appropriate to remove the cation to obtain free, biologically active protein.

2. A method of claim 1, wherein the vitamin K-dependent protein comprises activated human protein C.

3. A method of claim 1, wherein the vitamin K-dependent protein comprises human protein C zymogen.

4. A method of claim 1, wherein the vitamin K-dependent protein comprises human protein S.

5. A method of claim 1, wherein the removal of divalent cations in (a) comprises adding a chelating agent to the medium.

6. A method of claim 1, wherein the divalent cation is selected from the group consisting of ionic calcium, barium and strontium.

7. A method of claim 1, wherein the protein-binding anion-exchange resin comprises an cationic amine-based anion-exchange resin.

8. A method of claim 1, wherein the treatment of the cation-protein complex in (d) comprises combining a chelating agent with the complex.

9. A method for purifying vitamin K-dependent proteins from a cell culture medium of transformed cells which produce recombinant vitamin K-dependent proteins, comprising the steps of:
   (a) combining the cell culture medium containing the proteins with a chelating agent sufficient to remove endogenous divalent cations from the medium;
   (b) contacting the mixture from (a) with the anion-exchange material under conditions appropriate to effect binding of the proteins to the anion-exchange material;
   (c) contacting the protein-bound anion-exchange material from (b) with a source of divalent cation under conditions appropriate to form a cation-protein complex and to thereby dissociate the protein from the anion-exchange material;
   (d) contacting the cation-protein complex formed in (c) with chelating material under conditions appropriate to remove the cations from the complex thereby obtaining free protein;
   (e) purifying the protein obtained in (d) by contacting the protein with a second ion exchange material under conditions appropriate to effect binding of the protein to the ion-exchange material;
   (f) contacting the protein-bound ion-exchange material from (e) with a monovalent salt under conditions appropriate to dissociate the protein from the ion-exchange material;
   (g) contacting the protein obtained in (f) with a divalent cation sufficient to form a cation-protein complex;
   (h) contacting the cation-protein complex obtained in (g) with a hydrophobic material under conditions appropriate to effect binding of the cation-protein complex to the hydrophobic material; and
   (i) contacting a chelating agent with the protein-bound hydrophobic material of (h) under conditions appropriate to remove the cations from the cation-protein complex and to thereby dissociate the protein from the hydrophobic material.

10. A method of claim 9, wherein the divalent cation is selected from the group consisting of ionic calcium, barium and strontium.

11. A method of claim 9, wherein the protein comprises activated human protein C.

12. A method of claim 9, wherein the protein comprises human protein C zymogen.

13. A method of claim 9, wherein the protein comprises human protein S.

14. A method of claim 9, wherein the chelating agent comprises EDTA.

15. A method of claim 9, wherein the anion-exchange material of (b) comprises an cationic amine-based anion-exchange resin.

16. A method of claim 13, wherein said cationic amine-based anion-exchange resin is packed into a column.

17. A method of claim 9, wherein the chelating material of (d) comprises a resin having EDTA immobilized thereon.

18. A method of claim 17, wherein the chelating resin is packed into a column.

19. A method of claim 9, wherein the ion-exchange material of (e) comprises an cationic amine-based anion-exchange resin.

20. A method of claim 19, wherein said cationic amine-based anion-exchange resin is packed into a column.

21. A method of claim 9, wherein the monovalent salt of (f) comprises sodium chloride having a concentration between about 0.4 M to about 1.0 M.

22. A method of claim 9, wherein the hydrophobic material of (h) is selected from the group consisting of phenyl superose resin and phenyl sepharose resin.

23. A method for separating high-specific-activity vitamin K-dependent proteins from low-specific-activity vitamin K-dependent proteins contained in a cell culture medium of transformed cells which produce recombinant vitamin K-dependent proteins, comprising the steps of:
(a) combining the cell culture medium containing the proteins with an amount of EDTA sufficient to remove endogenous calcium from the medium;
(b) contacting the mixture obtained in (a) with an anion-exchange resin under conditions appropriate to effect binding of the proteins to the ion-exchange resin;
(c) contacting the protein-bound anion-exchange resin in (b) with a source of calcium ions under conditions appropriate to form a calcium-protein complex and to thereby dissociate the protein from the anion-exchange material;
(d) contacting the calcium-protein complex formed in (c) with a resin material having EDTA immobilized thereon, under conditions appropriate to remove the calcium ions from the complex thereby obtaining free protein;
(e) purifying the protein obtained in (d) by contacting the protein with a second ion-exchange resin under conditions appropriate to effect binding of the protein to the ion-exchange resin;
(f) contacting the protein-bound ion-exchange material from (e) with a monovalent salt under conditions appropriate to dissociate the protein from the ion-exchange resin;
(g) contacting the protein obtained in (e) with a source of calcium ions sufficient to form a cation-protein complex;
(h) contacting the calcium-protein complex obtained in (g) with a hydrophobic resin under conditions appropriate to effect binding of the calcium-protein complex to the hydrophobic resin; and
(i) contacting the protein-bound hydrophobic material of (h) with an amount of EDTA sufficient to remove the calcium from the calcium-protein complex and to thereby selectively dissociate the high-specific activity protein from the hydrophobic resin.

24. A method of claim 23, wherein the vitamin K-dependent protein comprises activated human protein C.

25. A method of claim 23, wherein the vitamin K-dependent protein comprises human protein C zymogen.

26. A method of claim 23, wherein the vitamin K-dependent protein comprises human protein S.

27. A method of claim 23, wherein the ion-exchange resin of (b) comprises an cationic amine-based anion-exchange resin.

28. A method of claim 23, wherein the hydrogen resin of (g) is selected from the group consisting of phenyl superose and phenyl sepharose.

29. A method of claim 23, wherein the monovalent salt of (f) comprises sodium chloride having a concentration between about 0.4 to about 1.0 M.

30. A method for recovering and purifying vitamin K-dependent proteins from a cell culture medium of cells which produce vitamin K-dependent proteins, comprising:
(a) removing divalent cations from the medium;
(b) contacting the medium with a protein-binding anion-exchange resin under conditions such that the protein is bound to the resin;
(c) treating the resin-bound protein with a divalent cation under conditions appropriate to form a cation-protein complex and to thereby dissociate the protein from the resin; and
(d) treating the cation-protein complex under conditions appropriate to remove the cation to obtain free, biologically active protein.

31. A method of claim 30, wherein the protein is selected from the group consisting of human protein C, human protein C zymogen, and human protein S.

32. A method for purifying vitamin K-dependent proteins from a cell culture medium of cells which produce vitamin K-dependent proteins, comprising the steps of:
(a) combining the cell culture medium containing the proteins with a chelating agent sufficient to remove endogenous divalent cations from the medium;
(b) contacting the mixture from (a) with an anion-exchange material under conditions appropriate to effect binding of the proteins to the anion-exchange material;
(c) contacting the protein-bound protein anion-exchange material from (b) with a source of divalent cation under conditions appropriate to form a cation-protein complex and to thereby dissociate the protein from the anion-exchange material;
(d) contacting the cation-protein complex formed in (c) with chelating material under conditions appropriate to remove the cations from the complex thereby obtaining free protein;
(e) purifying the protein obtained in (d) by contacting the protein with a second ion exchange material under conditions appropriate to effect binding of the protein to the ion-exchange material;
(f) contacting the protein-bound ion-exchange material from (e) with a monovalent salt under conditions appropriate to dissociate the protein from the ion-exchange material;
(g) contacting the protein obtained in (f) with a divalent cation sufficient to form a cation-protein complex;
(h) contacting the cation-protein complex obtained in (g) with a hydrophobic material under conditions appropriate to effect binding of the cation-protein complex to the hydrophobic material; and
(i) contacting a chelating agent with the protein-bound hydrophobic material of (h) under conditions appropriate to remove the cations from the cation-protein complex and to thereby dissociate the protein from the hydrophobic material.

33. A method of claim 32, wherein the divalent cation is selected from the group consisting of ionic calcium, barium, and strontium.

34. A method of claim 33, wherein the protein is selected from the group consisting of activated human protein C, human protein C zymogen, and human protein S.

35. A method for separating high-specific-activity vitamin K-dependent proteins from low-specific-activity vitamin K-dependent proteins contained in a cell culture medium of cells which produce vitamin K-dependent proteins, comprising the steps of:
  (a) combining the cell culture medium containing the proteins with an amount of EDTA sufficient to remove endogenous calcium from the medium;
  (b) contacting the mixture obtained in (a) with an anion-exchange resin under conditions appropriate to effect binding of the proteins to the anion-exchange resin;
  (c) contacting the protein-bound anion-exchange resin in (b) with a source of calcium ions under conditions appropriate to form a calcium-protein complex and to thereby dissociate the protein from the anion-exchange material;
  (d) contacting the calcium-protein complex formed in (c) with a resin material having EDTA immobilized thereon, under conditions appropriate to remove the calcium ions from the complex thereby obtaining free protein;
  (e) purifying the protein obtained in (d) by contacting the protein with a second ion-exchange resin under conditions appropriate to effect binding of the protein to the ion-exchange resin;
  (f) contacting the protein-bound ion-exchange material from (e) with a monovalent salt under conditions appropriate to dissociate the protein from the ion-exchange material;
  (g) contacting the protein obtained in (f) with a source of calcium ions sufficient to form a calcium-protein complex;
  (h) contacting the calcium-protein complex obtained in (g) with a hydrophobic resin under conditions appropriate to effect binding of the calcium-protein complex to the hydrophobic resin; and
  (i) contacting the protein-bound hydrophobic material of (h) with an amount of EDTA sufficient to remove the calcium from the calcium-protein complex and to thereby selectively dissociate the high-specific activity protein from the hydrophobic resin.

36. A method of claim 35, wherein the calcium-binding protein comprises activated human protein C.

37. A method of claim 35, wherein the protein is human protein C zymogen.

38. A method of claim 35, wherein the protein comprises human protein S.

39. A method for removing non-proteinaceous contaminants from a sample of vitamin K-dependent proteins, said method comprising the steps of:
  (a) removing divalent cations from the sample;
  (b) contacting the sample with a protein-binding anion-exchange resin under conditions such that the protein is bound to the resin;
  (c) treating the resin-bound protein with a divalent cation under conditions appropriate to form a cation-protein complex and to thereby dissociate the protein from the resin; and
  (d) treating the cation-protein complex under conditions appropriate to remove the cation to obtain free, biologically active protein.

40. A method of claim 39, wherein the vitamin K-dependent protein comprises activated human protein C.

41. A method of claim 39, wherein the vitamin K-dependent protein comprises human protein C zymogen.

42. A method of claim 39, wherein the vitamin K-dependent protein comprises human protein S.

43. A method of claim 39, wherein the non-proteinaceous contaminant is a bacterial endotoxin.

44. A method for removing viral contaminants from a sample of vitamin K-dependent proteins, said method comprising the steps of:
  (a) removing divalent cations from the sample;
  (b) contacting the sample with a protein-binding anion-exchange resin under conditions such that the protein is bound to the resin;
  (c) treating the resin-bound protein with a divalent cation under conditions appropriate to form a cation-protein complex and to thereby dissociate the protein from the resin; and
  (d) treating the cation-protein complex under conditions appropriate to remove the cation to obtain free, biologically active protein.

45. A method of claim 44, wherein the vitamin K-dependent protein comprises activated human protein C.

46. A method of claim 44, wherein the vitamin K-dependent protein comprises human protein C.

47. A method of claim 44, wherein the vitamin K-dependent protein comprises human protein S.

* * * * *

UNITED STATES PATENT AND TRADEMARK OFFICE
CERTIFICATE OF CORRECTION

PATENT NO. : 4,981,952

DATED : January 1, 1991

INVENTOR(S) : S. Betty Yan

It is certified that error appears in the above-identified patent and that said Letters Patent is hereby corrected as shown below:

Col. 16
In Claim 7, delete "cationic."

In Claim 15, delete "cationic."

In Claim 16, delete "cationic."
Col. 17
In Claim 19, delete "cationic."

In Claim 20, delete "cationic."
Col. 18
In Claim 27, delete "cationic."

In Claim 28, change "hydrogen" to -- hydrophobic --.

In Claim 32, after "protein-bound," delete "protein."
Col. 20
In Claim 46, after "protein C," insert -- zymogen --.

Signed and Sealed this

Twenty-second Day of December, 1992

Attest:

DOUGLAS B. COMER

Attesting Officer      Acting Commissioner of Patents and Trademarks